US 7,547,506 B2

(12) United States Patent
Surujballi et al.

(10) Patent No.: US 7,547,506 B2
(45) Date of Patent: Jun. 16, 2009

(54) **PEPTIDE-BASED FLUORESCENCE POLARIZATION ASSAY FOR DETECTION OF ANTIBODIES TO *MYCOBACTERIUM BOVIS***

(75) Inventors: Om P. Surujballi, Nepean (CA); Anna Romanowska, Ottawa (CA); Michael E. Jolley, Round Lake, IL (US); Mohammad Sarwar Nasir, Grayslake, IL (US)

(73) Assignees: Diachemix LLC, Milwaukee, WI (US); Her Majesty the Queen in Right of Canada, as represented by the Canadian Food Inspection Agency, Ottawa (Nepean), Ontario (CA)

( * ) Notice: Subject to any disclaimer, the term of this patent is extended or adjusted under 35 U.S.C. 154(b) by 649 days.

(21) Appl. No.: 10/492,998

(22) PCT Filed: Oct. 31, 2002

(86) PCT No.: PCT/US02/34964

§ 371 (c)(1),
(2), (4) Date: Apr. 19, 2004

(87) PCT Pub. No.: WO03/038402

PCT Pub. Date: May 8, 2003

(65) Prior Publication Data

US 2004/0214250 A1    Oct. 28, 2004

Related U.S. Application Data

(60) Provisional application No. 60/335,368, filed on Oct. 31, 2001.

(51) Int. Cl.
*C12Q 1/00* (2006.01)
*A61K 39/04* (2006.01)
*G01N 33/566* (2006.01)
*A61K 38/00* (2006.01)

(52) U.S. Cl. .................. 435/4; 435/7.1; 435/253.1; 436/501; 436/543; 436/546; 530/300; 530/350; 424/9.1; 424/9.2; 424/130.1; 424/150.1; 424/164.1; 424/184.1; 424/248.1

(58) Field of Classification Search .................. 424/9.1, 424/9.2, 130.1, 139.1, 150.1, 164.1, 184.1, 424/248.1; 435/4, 7.1, 253.1; 436/501, 543, 436/546; 530/300, 350
See application file for complete search history.

(56) References Cited

U.S. PATENT DOCUMENTS

| | | | | |
|---|---|---|---|---|
| 5,635,346 A | * | 6/1997 | Leahy et al. | .................. 435/5 |
| 5,693,500 A | * | 12/1997 | Wood et al. | .................. 435/69.3 |
| 5,976,820 A | | 11/1999 | Jolley et al. | |
| 6,110,750 A | * | 8/2000 | Sugden et al. | .................. 436/537 |
| 6,350,574 B1 | | 2/2002 | Montelaro et al. | |
| 6,596,546 B1 | | 7/2003 | Jolley et al. | |

FOREIGN PATENT DOCUMENTS

| | | |
|---|---|---|
| WO | 97/08559 A1 | 3/1997 |
| WO | 00/17649 A1 | 3/2000 |

OTHER PUBLICATIONS

Lin, M., et al. Modification of the Mycobacterium bovis extracellular protein MPB70 with fluorescein for rapid detection of specific serum antibodies by fluorescence polarization. Clinical and Diagnostic Laboratory Immunology, vol. 3. pp. 438-443, 1996.*
Dicttionary of Biochemistry and Molecular Biology, second edition, J. Stenesh, ed., John Wiley & Sons, New York, 1989, p. 351.*
Lin et al, Clinical and Diagnostic Laboratory Immunology, vol. 3, pp. 438-443, 1996.*
Nasir, et al., "Fluorescence Polarization: An Analytical Tool for Immunoassay and Drug Discovery," *Combinatorial Chemistry & High Throughput Screening*, 1999, 2, 177-190.
Written Opinion, International application No. PCT/US02/34964, Oct. 22, 2004.
*Concise Encyclopedia Chemistry*, Walter de Gruyter 1994, pp. 785-787.
*The Columbia Encyclopedia* (6th ed. 2000), pp. 2182-2183.
K.A. Lightbody, et al., "IgG isotype antibody responses to epitopes of the *Mycobacterium bovis* protein MPB70 in immunized and in tuberculin skin test reactor cattle," *Veterinary Microbiology*, vol. 25, pp. 177-188 (2000).
Harald G. Wiker, et al., "Immunochemical Characterization of the MPB70/80 and MPB83 Proteins of *Mycobacterium bovis*," *Infection and Immunity*, vol. 66, pp. 1445-1452 (1998).
Om P. Surujballi, et al., "A fluorescence polarization assay for the detection of antibodies to *Mycobacterium bovis* in cattle sera," *Veterinary Microbiology*, vol. 87, pp. 149-157 (2002).
Communication, dated Nov. 13, 2008, from related European Application No. 02 802 505.4.

* cited by examiner

*Primary Examiner*—Rodney P. Swartz
(74) *Attorney, Agent, or Firm*—McDonnell Boehnen Hulbert & Berghoff LLP

(57) ABSTRACT

The present invention provides an assay for detection of *M. bovis*-infected animals. A tracer, comprising a peptide of *M. bovis* protein MPB70 conjugated to a fluorophore, is added to a serum sample from an animal to form a mixture. The fluorescence polarization of the mixture in then measured and compared to the fluorescence polarization of a control. The present invention further provides a tracer for use in fluorescence polarization assay to detect antibodies specific for *M. bovis*. The tracer comprises a peptide of *M. bovis* protein MPB70 conjugated to a fluorophore, such that the tracer is able to bind to antibodies specific for *M. bovis* to produce a detectable change in fluorescence polarization.

9 Claims, No Drawings

PEPTIDE-BASED FLUORESCENCE POLARIZATION ASSAY FOR DETECTION OF ANTIBODIES TO *MYCOBACTERIUM BOVIS*

CROSS REFERENCE TO RELATED APPLICATIONS

This application claims priority from U.S. patent application Ser. No. 60/335,368, filed Oct. 31, 2001. All patents, patent applications, as well as all other scientific and/or technical writings referred to herein are incorporated by reference to the extent that they are not contradictory.

BACKGROUND OF THE INVENTION

1. Field of the Invention

This invention relates to the field of diagnostic assays. More particularly, this invention relates to a peptide-based assay that uses changes in fluorescence polarization to detect serum antibodies to *Mycobacterium bovis*.

2. Description of Related Art

Fluorescence polarization is a well-known technique that has been used for a number of applications, including animal disease diagnostics, detection of food-borne pathogens, and grain mycotoxin determination. See M. S. Nasir, M. E. Jolley (1999) "Fluorescence Polarization: An analytical tool for Immunoassay and Drug Discovery." *Combinatorial Chemistry & High Throughput Screening*, vol. 2, pp. 177–190. The overall strengths of fluorescence polarization tests lie in the simplicity, ease, rapidity, and cost-effectiveness of the tests protocols. For example, fluorescence polarization tests typically do not require washing steps.

In general, a fluorescence polarization test for disease detection is run as follows. A small quantity of sample is added into a tube containing a buffer solution. A blank is read in the instrument. A fluorescent tracer specific for the disease is added in the same tube and the resultant polarization value is noted within seconds to minutes.

U.S. Pat. No. 6,110,750, which is fully incorporated herein by reference, disclosed a fluorescence polarization technique for detection of animals infected with *Mycobacterium bovis*. The technique was based on the MPB70 protein secreted by *M. bovis*. The MPB70 protein was considered to be a highly species-specific immunodominant antigen containing at least three separate *M. bovis*-specific epitopes. The fluorescence polarization technique used a tracer comprising MPB70 protein conjugated to a fluorophore to detect antibodies to *M. bovis* in sera from animals, such as cattle, bison, llama, and elk.

However, in order to increase the potential sensitivity of fluorescence polarization assays for *M. bovis* infection, it is desirable to develop fluorescence tracers based on molecules smaller than MPB70.

SUMMARY OF THE INVENTION

In a first principal aspect, the present invention provides an assay for detection of *M. bovis*-infected animals. A tracer, comprising a peptide of *M. bovis* protein MPB70 conjugated to a fluorophore, is added to a serum sample from an animal to form a mixture. The fluorescence polarization of the mixture is then measured. The presence of *M. bovis* antibodies in the animal is detected from the measured fluorescence polarization of the mixture.

In a second principal aspect, the present invention provides a tracer for use in a fluorescence polarization assay for antibodies specific for *M. bovis*. The tracer comprises a peptide of *M. bovis* protein MPB70 conjugated to a fluorophore, such that the tracer is able to bind to antibodies specific for *M. bovis* to produce a detectable change in fluorescence polarization.

DETAILED DESCRIPTION OF THE PREFERRED EMBODIMENTS

A number of different peptides of MPB70 were screened for their suitability to detect serum antibodies to *M. bovis* using fluorescence polarization. Specific examples are described herein.

EXAMPLE 1

A peptide with the following amino acid sequence was manufactured: PTNAAFSKLPASTIDELKTN (Pro Thr Asn Ala Ala Phe Ser Lys Leu Pro Ala Ser Thr Ile Asp Glu Leu Lys Thr Asn) (Ref. No.: 554; SEQ. ID NO.: 1).

The peptide was then labeled in the following manner. The peptide was dissolved (2 mg/ml) in 1M sodium bicarbonate pH 8.3 at room temperature. A dye, 5-carboxyfluorescein succinimidyl ester (5-FAM, SE, Molecular Probes, Oregon) was then dissolved (10 mg/ml) in dimethyl sulfoxide (DMSO, Sigma-Aldrich Canada, Oakville, Ontario, Canada) and a sufficient quantity was added to the peptide solution to yield a dye:peptide molar ratio of 1:1. The mixture was stirred for 1 hour at room temperature in the dark. Hydroxylamine buffered to pH 8.5 (Molecular Probes) was added to the mixture and the stirring was continued for an additional 30 minutes. The mixture was then added to a Sephadex G-25 fine column (1×50 cm), which was pre-equilibrated with phosphate buffered saline (PBS, 0.01 M sodium phosphate+ 0.85% sodium chloride, pH 7.2) supplemented with 0.02% sodium azide. The labeled peptide was separated from the free dye by elution with PBS. Fractions (1 ml) were collected and the absorbance monitored at 492 nm. The elution profile showed 2 well separated peaks, the first of which contained the fluorescently-labeled peptide. The fractions containing the first peak were then pooled and concentrated using an Amicon Ultrafiltration Cell (Millipore, Corporation, Nepean, Ontario, Canada) fitted with an Amicon YM-1 membrane (Millipore).

This labeled peptide was then tested for its suitability used as a fluorescent tracer for detecting serum antibodies to *M. bovis*. Specifically, the labeled peptide was tested by adding it to serum samples from cattle, elk, and deer, some of which were known positives for *M. bovis* infection and some of which were known negatives for *M. bovis* infection. It was found that the positive and negative sera gave different fluorescence polarization measurements after labeled peptide was added. Thus, it was determined that this labeled peptide can be used to detect serum antibodies to *M. bovis*.

EXAMPLE 2

A peptide with the following amino acid sequence was manufactured: SVQGMSQDPVAVAASNNPEL (Ser Val Gln Gly Met Ser Gln Asp Pro Val Ala Val Ala Ala Ser Asn Asn Pro Glu Leu) (Ref. No.: 555; SEQ. ID NO.: 2).

This peptide was labeled and purified using the procedures described in Example 1, except that a different dye, fluorescein-5-EX, succinimidyl ester (Molecular Probes) was used, and the dye:peptide molar ratio was 20:1. This dye compound has a succinimidyl reactive group that is separated from the fluorophore by a seven atom spacer. This spacer serves to minimize interaction between the fluorophore and the amino acids to which the dye is conjugated.

This labeled peptide was then tested as described above for Example 1. It was found that this labeled peptide can also be used to detect serum antibodies to *M. bovis,* i.e., that positive and negative sera gave different fluorescence polarization measurements upon addition of the labeled peptide.

EXAMPLE 3

The MPB70 protein was epitope scanned to make small fluorescent peptides. Epitope scanning was accomplished using a Multipin™ Peptide Synthesis block (cleavable DKP, Catalog No. KT-96-0-DKP, batch no. 1252-2A) consisting of 96 gears, which was purchased from Mimotypes Pty Ltd., Calyton, Victoria, Australia. Specifically, this kit was used, in accordance with the Multipin™ instructions, to synthesize 96 peptides of 15 amino acids each, each corresponding to a peptide of MPB70. After synthesis, each peptide was covalently attached with 6-carboxyfluorescein (isomer 2). The gears were then washed with excess DMF and methanol, and the resultant block was immersed overnight in a 96 deep well (1 ml capacity, with each well containing 800 microliters of 0.1 M phosphate:$CH_3CN$ (60:40) solution) to obtain solutions of free labeled peptide.

The free labeled peptide solutions were then diluted appropriately for conducting fluorescence polarization assays. Each labeled peptide was tested by adding it to cattle sera, both positive and negative for *M. bovis,* and measuring the resulting fluorescence polarization. In this way, it was found that two labeled peptides could be used to detect serum antibodies to *M. bovis,* i.e., that positive and negative sera gave different fluorescence polarization measurements upon addition of the labeled peptide. Two promising peptides had the following amino acid sequences: AVAASNNPELTTLTA (Ala Val Ala Ala Ser Asn Asn Pro Glu Leu Thr Thr Leu Thr Ala) (SEQ. ID NO.: 3) and PTNAAFSKLPASTID (Pro Thr Asn Ala Ala Phe Ser Lys Leu Pro Ala Ser Thr Ile Asp) (SEQ. ID NO.: 4).

EXAMPLE 4

Additional peptides were generated and labeled essentially as described above. The peptides were labeled with 6-carboxyfluorescein (6-FAM or 6-fam; Sigma-Aldrich # 54115; Molecular Probes #C-1360 or #C-6164 (6-FAM, succinimidyl ester)). The sequences of the peptides were:

```
6-fam-GMSQDPVAVAASNNPELTTLTAALS;      (Ref. No.: 708; SEQ. ID NO.: 5)

and 6-fam-SVQGMSQDPVAVAASNNPELTTLTAALS.   (Ref. No.: 799, SEQ. ID NO.: 6)
```

The peptides, as well as the full-length MPB70 protein, were used in fluorescence polarization assays as described above to screen sera from *Mycobacterium bovis*-infected animals as well as non-infected animals. The fluorescence polarization assays were positive for *Mycobacterium bovis* infection when the measured fluorescence polarization exceeded a predetermined threshold value. The charts below summarize the results from these assays:

| SERUM SOURCE | # of SERA | Classification | MPB70 Sens. % | MPB70 Spec. % | Peptide 555 Sens. % | Peptide 555 Spec. % | Peptide 708 Sens. % | Peptide 708 Spec. % | Peptide 799 Sens. % | Peptide 799 Spec. % | Peptide 554 Sens. % | Peptide 554 Spec. % |
|---|---|---|---|---|---|---|---|---|---|---|---|---|
| North America Canada | 5666 | Presumed negative | | | 98.3 (5570/5666) | | | | | | | |
| | 28 | Culture positive | 92.9 (26/28) | | | | | | | | | |
| #1 | 50 | Skin test positive | 36 (18/50) | N.D. | | | 76 (38/50) | N.D. | | | | |
| #2 | 90 | 17 skin test positive 73 skin test negative | 64.7 (11/17) | 98.6 (72/73) | | | 82.4 (14/17) | 97.3 (71/73) | | | | |
| #3 | 49 | Lesion positive | 55.1 (27/49) | N.D. | | | 61.2 (30/49) | N.D. | 67.3 (33/49) 71.4 (35/49) (peptides 555 + 799) | | 51.0 (25/49) 71.4 (35/49) (peptides 555 + 554 + 799) | |
| North America Ontario 02 | 557 | Presumed negative | | | 98.75 (550/557) | | | | | | 98.75 (550/557) | |
| | 69 | 65 skin test positive 4 skin test | | | | | 55.4 (36/65) | 25 (1/4) | | | 5/63 | |

-continued

| SERUM SOURCE | # of SERA | Classification | MPB70 Sens. % | Spec. % | Peptide 555 Sens. % | Spec. % | Peptide 708 Sens. % | Spec. % | Peptide 799 Sens. % | Spec. % | Peptide 554 Sens. % | Spec. % |
|---|---|---|---|---|---|---|---|---|---|---|---|---|
| | | negative | | | | | | | | | (1 unique) 58 (40/69) (peptides 708 + 554) | |
| | 48 | Lesion positive | 56.3 (27/48) | | 71.4 (30/42) | | 64.4 (29/45) | | 68.8 (33/48) 72.9 (35/48) (peptides 708 + 799) | | 46.5 (25/48) | |

The foregoing description of the invention is presented for purposes of illustration and description, and is not intended, nor should be construed, to be exhaustive or to limit the invention to the precise forms disclosed. The description was selected to best explain the principles of the invention and practical application of these principles to enable others skilled in the art to best utilize the invention in various embodiments and with various modifications as are suited to the particular use contemplated. It is intended that the scope of the invention not be limited by the specification, but defined by the claims.

We claim:

1. A method for detecting *M. bovis*-infected animals, the method comprising:
adding a tracer to a sample from an animal to form a mixture, wherein the tracer is formed by labeling a polypeptide of *M. bovis* protein MPB70 with a fluorophore, and wherein the polypeptide consists of an amino acid sequence selected from the group consisting of SEQ. ID NO.:2 and SEQ. ID NO.:6;
measuring the fluorescence polarization of the mixture;
measuring the fluorescence polarization of a control;
comparing the fluorescence polarization of the mixture to the fluorescence polarization of the control; and
detecting the presence of *M. bovis* antibodies in the animal from the measured fluorescence polarization of the mixture.

2. The method of claim 1, wherein the sample is serum.

3. The method of claim 1, wherein the fluorophore is fluorescein or a derivative thereof.

4. A tracer for detecting *M. bovis* antibodies in the fluorescence polarization assay, wherein the tracer is formed by labeling a polypeptide of *M. bovis* protein MPB70 with a fluorophore, wherein the polypeptide consists of an amino acid sequence selected from the group consisting of SEQ. ID NO.:2 and SEQ. ID NO.:6, such that the tracer binds to antibodies specific for *M. bovis* to produce a detectable change in fluorescence polarization.

5. The tracer of claim 4, wherein the amino acid sequence of the polypeptide is: SVQGMSQDPVAVAASNNPEL (Ser Val Gln Gly Met Ser Gln Asp Pro Val Ala Val Ala Ala Ser Asn Asn Pro Glu Leu) (SEQ. ID NO.: 2).

6. The tracer of claim 4, wherein the fluorophore is 6-carboxyfluoroscein.

7. The tracer of claim 4, wherein the amino acid sequence of the polypeptide is: SVQGMSQDPVAVAASNNPELTTLTAALS (SEQ. ID NO.: 6).

8. The tracer of claim 7, wherein the fluorophore is 6-carboxyfluoroscein.

9. A kit for detecting *M. bovis* antibodies in a sample taken from an animal, wherein the antibodies are detected using fluorescence polarization and the kit comprises a tracer as in claim 4.

* * * * *

```
                        SEQUENCE LISTING

<160> NUMBER OF SEQ ID NOS: 6

<210> SEQ ID NO 1
<211> LENGTH: 20
<212> TYPE: PRT
<213> ORGANISM: Mycobacterium bovis

<400> SEQUENCE: 1

Pro Thr Asn Ala Ala Phe Ser Lys Leu Pro Ala Ser Thr Ile Asp Glu
1               5                   10                  15

Leu Lys Thr Asn
            20

<210> SEQ ID NO 2
<211> LENGTH: 20
<212> TYPE: PRT
<213> ORGANISM: Mycobacterium bovis

<400> SEQUENCE: 2

Ser Val Gln Gly Met Ser Gln Asp Pro Val Ala Val Ala Ala Ser Asn
1               5                   10                  15

Asn Pro Glu Leu
            20

<210> SEQ ID NO 3
<211> LENGTH: 15
<212> TYPE: PRT
<213> ORGANISM: Mycobacterium bovis

<400> SEQUENCE: 3

Ala Val Ala Ala Ser Asn Asn Pro Glu Leu Thr Thr Leu Thr Ala
1               5                   10                  15

<210> SEQ ID NO 4
<211> LENGTH: 15
<212> TYPE: PRT
```

```
<213> ORGANISM: Mycobacterium bovis

<400> SEQUENCE: 4

Pro Thr Asn Ala Ala Phe Ser Lys Leu Pro Ala Ser Thr Ile Asp
1               5                   10                  15

<210> SEQ ID NO 5
<211> LENGTH: 25
<212> TYPE: PRT
<213> ORGANISM: Mycobacterium bovis
<220> FEATURE:
<221> NAME/KEY: misc_feature
<222> LOCATION: (1)..(1)
<223> OTHER INFORMATION: labeled at the amino terminus with 6-FAM

<400> SEQUENCE: 5

Gly Met Ser Gln Asp Pro Val Ala Val Ala Ala Ser Asn Asn Pro Glu
1               5                   10                  15

Leu Thr Thr Leu Thr Ala Ala Leu Ser
            20                  25

<210> SEQ ID NO 6
<211> LENGTH: 28
<212> TYPE: PRT
<213> ORGANISM: Mycobacterium bovis
<220> FEATURE:
<221> NAME/KEY: misc_feature
<222> LOCATION: (1)..(1)
<223> OTHER INFORMATION: labeled at the amino terminus with 6-FAM

<400> SEQUENCE: 6

Ser Val Gln Gly Met Ser Gln Asp Pro Val Ala Val Ala Ala Ser Asn
1               5                   10                  15

Asn Pro Glu Leu Thr Thr Leu Thr Ala Ala Leu Ser
            20                  25
```